(12) United States Patent
Guy et al.

(10) Patent No.: US 9,205,063 B2
(45) Date of Patent: *Dec. 8, 2015

(54) CANNABINOID-CONTAINING PLANT EXTRACTS AS NEUROPROTECTIVE AGENTS

(71) Applicant: GW Pharma Limited, Salisbury (GB)

(72) Inventors: Geoffrey Guy, Salisbury (GB); Bettina Platt, Aberdeen (GB)

(73) Assignee: GW Pharma Limited, Salisbury, Wiltshire (GB)

( * ) Notice: Subject to any disclaimer, the term of this patent is extended or adjusted under 35 U.S.C. 154(b) by 11 days.

This patent is subject to a terminal disclaimer.

(21) Appl. No.: 14/163,019

(22) Filed: Jan. 24, 2014

(65) Prior Publication Data

US 2014/0377382 A1    Dec. 25, 2014

Related U.S. Application Data

(63) Continuation of application No. 12/087,847, filed as application No. PCT/GB2007/000122 on Jan. 17, 2007, now Pat. No. 8,673,368.

(30) Foreign Application Priority Data

Jan. 18, 2006  (GB) .................................. 0601013.6

(51) Int. Cl.
| | |
|---|---|
| A01N 65/00 | (2009.01) |
| A61K 31/05 | (2006.01) |
| A61K 36/00 | (2006.01) |
| A61K 31/352 | (2006.01) |
| A61K 36/185 | (2006.01) |

(52) U.S. Cl.
CPC .............. *A61K 31/05* (2013.01); *A61K 31/352* (2013.01); *A61K 36/00* (2013.01); *A61K 36/185* (2013.01)

(58) Field of Classification Search
CPC ........................................................ A61K 36/00
USPC ....................................................... 424/725
See application file for complete search history.

(56) References Cited

U.S. PATENT DOCUMENTS

| 8,673,368 B2 | 3/2014 | Guy et al. |
| 2004/0034108 A1 | 2/2004 | Whittle |
| 2005/0070596 A1 | 3/2005 | Baker et al. |
| 2006/0039959 A1 | 2/2006 | Wessling |
| 2010/0239693 A1 | 9/2010 | Guy et al. |
| 2014/0228438 A1 | 8/2014 | Iuvone et al. |

FOREIGN PATENT DOCUMENTS

| GB | WO 02/32420 A1 | 4/2002 |
| GB | 2 376 464 A | 12/2002 |
| GB | 2 337 633 A | 1/2003 |
| GB | 2 391 865 A | 2/2004 |
| GB | 2 392 093 A | 2/2004 |
| GB | 2 434 312 A | 7/2007 |
| GB | 2 450 493 A | 12/2008 |
| GB | 2 479 153 A | 10/2011 |
| WO | WO 02/064109 A2 | 8/2001 |
| WO | WO 02/069993 A1 | 9/2002 |
| WO | WO 02/089945 A2 | 11/2002 |
| WO | WO 03/037306 a2 | 5/2003 |
| WO | WO 03/105800 A2 | 12/2003 |
| WO | WO 2004/016246 a1 | 2/2004 |
| WO | WO 2006/054057 A2 | 5/2006 |
| WO | WO 2008/024490 A2 | 2/2008 |
| WO | WO 2013/005017 A1 | 1/2013 |

OTHER PUBLICATIONS

[No Author Listed] Cannabinoid. Wikipedia. Version as edited on Jun. 28, 2007. http://en.wikipedia.org/wiki/Cannabinoid. 11 pages.
Ali Ibn-e-Abbaas Majoosi; Kaamil-al-Sena'ah, Part II (10th Century AD), Central Council for Research in Unani Medicine, 61-65 Institutional Area, Janak Puri, New Delhi-58, 2005AD, pp. 116.
Ayurveda Sarasamgrahah—Shri Baidyanath Ayurveda Bhavan Limited, Calcutta, Edn. 2003, pp. 467.
Berman et al., Efficacy of Two cannabis based medicinal extracts for relief of central neuropathic pain from brachial plexus avulsion: results of a randomised controlled trial. Pain. Dec. 2004;112(3):299-306.
Carroll et al., Cannabis for dyskinesia in Parkinson disease. A randomised double-blind crossover-study, Neurology 2004; 63:1245-1250.
Di Marzo et al., Plant, synthetic, and endogenous cannabinoids in medicne. Annu Rev Med. 2006;57:553-74.
Esposito et al., Cannabidiol in vivo blunts beta-amyloid induced neuroinflammation by suppressing IL-1beta and iNOS expression. Br J Pharmacol. Aug. 2007;151(8):1272-9. Epub Jun. 25, 2007.
Hampson et al., Cannabidiol and (-)Delta9-tetrahydrocannabinol are neuroprotective antioxidants. Proc Natl Acad Sci USA. Jul. 7, 1998;95(14);8268-73.
Hampson et al., Neuroprotective antioxidants from marijuana. Ann N Y Acad Sci. 2000;899:274-82. Review.
Hayakawa et al., Therapeutic Potential of Non-Psychotropic Cannabidiol in Ischemic Stroke. Pharmaceuticals. 2010: 3(7):2197-2212.
Iuvone et al., Cannabidiol: a Promising drug for neurodegenerative disorders? CNS Neurosci Ther. 2009 Winter;15(1):65-75. doi: 10.1111/j.1755-5949.2008.00065.x. Review.
Izzo et al., Non-psychotropic plant cannabinoids: new therapeutic opportunities from an ancient herb. Trends pharmacol Sci. Oct. 2009;30(10):515-27.

(Continued)

*Primary Examiner* — Michael Meller
(74) *Attorney, Agent, or Firm* — Wolf, Greenfield & Sacks, P.C.

(57) ABSTRACT

The invention relates to the use of cannabinoid-containing plant extracts in the prevention or treatment of neural degeneration. In particular, the invention relates to use of one or more cannabinoid-containing plant extracts in the prevention or treatment of neural degeneration, wherein the one or more cannabinoid-containing plant extracts comprise:
i) a cannabinoid-containing fraction; and
ii) a non-cannabinoid containing fraction.

1 Claim, No Drawings

(56) References Cited

OTHER PUBLICATIONS

Kichuk et al., Regulation of nitric oxide production in human coronary microvessels and the contribution of local kinin formation. Circulation. Jul. 1, 1996; 94(1):44-51.

Kuiper et al., Decreased cerebrospinal fluid nitrate levels in Parkinson's disease, Alzheimer's disease and multiple systems atrophy patients. J Neurol Sci. Jan. 1994;121(1):46-9.

Maksimović et al., Effects of nerve and fibroblast growth factors on the production of nitric oxide in experimental model of Huntington's disease. Vojnosanit Pregl. Mar.-Apr. 2002;59(2):119-23.

Mohammad Najmul Ghani Khan; Khazaain-al-advia, vol. I (20 th century AD), Nadeem Yunus Printer/Sheikh Mohd Basheer & Sons, Lahore, 1911 AD, pp. 886.

Mohammad Najmul Ghani Khan; Khazaain-al-Advia, vol. III (20$^{th}$ century AD), Nadeem Yunus Printer/Sheikh Mohd Basheer & Sons, Lahore, 1926 AD, pp. 77.

Rasatantrasarah Evam Siddhaprayogasamgrahah—part II; Krishan Gopal Ayurveda Bhawan; Edn 8$^{th}$; 1990; pp. 288-289.

The United Kingdom Parliament, Select Committee on Science and Technology Ninth Report (1998) at http://www.parliament.the-stationery-office.co.uk/pa/ld199798/1dselect/ldsctech/151/15101.htm.

The United Kingdom Parliament, Select Committee on Science and Technology second Report (Mar. 14, 2001) at http://www.publications.parliament.uk/pa/ld200001/ldselect/ldsctech/50/5001.htm.

Third Party Submission Under Art 37 CFR 1.99 "Patent publication No. 20100239693, filed on Jun. 4, 2010 & published on Sep. 23, 2010 with U.S. Appl. No. 12/087,847".

Vaney et al., Efficacy, safety and tolerability of an orally administered cannabis extract in the treatment of spasticity in patients with multiple sclerosis: a randomised, double-blind, placebo controlled, crossover study, Multiple Sclerosis 2004; 10:417-424.

Wade et al., A Preliminary controlled study to determine whether-plant cannabis extracts can improve intractable neurogenic symptoms, Clinical Rehabilitation 2003; 17:21-29.

Wade et al., Do cannabis-based medicinal extracts have general or specific effects on symptoms in multiple sclerosis? A double-blind, randomized, placebo-controlled study on 160 patients,38 Multiple Sclerosis 2004; 10:434-441.

Mohammad Azam Kha,n Muheet-e-Azam vol. III, 4 (p. No. 04-07), ( Ref.p. No. of publication:147), 1887 AD Matba, Nizami Kanpur, India.†

Manthana Bhairava, Anandakandh, 5 (p. No. 08-12), ( Ref.p. No. of publication:241 ), Edn. 1st 1952, T.M.S.S.M. Library. Tanjore, Madras. India.†

Rasatantrasarah Evam Siddhaprayogasamgrahah;—part II, 5 (p. No. 13-17 ), ( Ref.p. No. of publication:291-292 ), Edn 8th:1990, Krishan Gopal Ayurveda Bhawan, -, India.†

† cited by third party

CANNABINOID-CONTAINING PLANT EXTRACTS AS NEUROPROTECTIVE AGENTS

RELATED APPLICATIONS

This application is a continuation of U.S. application Ser. No. 12/087,847, filed Jun. 4, 2010, which is a national stage filing under 35 U.S.C. §371 of international application PCT/GB2007/000122, filed Jan. 17, 2007, which was published under PCT Article 21(2) in English, the contents of which are incorporated by reference in their entirety.

FIELD OF THE INVENTION

The present invention relates to the use of cannabinoid-containing plant extracts in the prevention or treatment of neural degeneration.

BACKGROUND TO THE INVENTION

Neural degeneration, or neurodegeneration, can be described as the progressive damage or death of neurones. Neurones are nerve cells in the brain whose primary function is to assist in the memory process. The damage or death of neurones leads to a gradual deterioration of the functions controlled by the affected part of the nervous system.

Neural degeneration often occurs as a result of oxidative stress. Oxidative stress occurs to the cells when the effects of pro-oxidants (such as free radicals, reactive oxygen and reactive nitrogen species) exceed the ability of anti-oxidants to neutralise them. When levels of free radicals or other pro-oxidants increase to such an extent, they can cause damage to cell membranes which in turn may result in cell death or damage to genetic material.

Neurodegenerative diseases are a group of disorders characterised by changes in normal neuronal functioning, leading, in most cases, to neuronal death. Most of these diseases are associated, especially in late stages, with severe neuronal loss.

With an ever increasing ageing population, progressively more individuals are affected by neurodegenerative diseases. According to the National Institute of Neurological Disorders and Stroke, there are more than 600 different types of neurological disorders.

Some of the most common types of neurological disorders include Alzheimer's disease, Parkinson's disease and multiple sclerosis.

The process of neural degeneration is often the result of glutamate excitotoxicity. Glutamate is a signalling chemical and under normal conditions the concentration of glutamate in a cell tends to be quite low. Glutamate is required at these low concentrations for crucial brain functions such as memory and learning. When glutamate concentrations increase, the process of neural degeneration begins.

When the brain is deprived of oxygen either due to a disease, such as a neurodegerative disease, a trauma, such as a closed head injury or due to an ischemic event such as a stroke, an abnormal build-up of glutamate occurs.

Neural degeneration takes place when glutamate attaches to receptor proteins on a cells surface. These N-methyl-D-aspartate (NMDA) receptors then open an excess of calcium channels causing the intracellular concentration of calcium to increase rapidly. Calcium ions activate phospholipase A (PLA), which in turn results in the release of arachidonic acid and superoxide radicals.

Neural degeneration continues from the destructive effects of oxidative radicals caused by the glutamate flood. The radicals cause disruption of essential reactions in the neurones and this leads to degeneration or death of the cell.

Neuroprotective agents that are able to block the NMDA receptor are useful as they are able to block the reaction caused by glutamate and therefore prevent neural degeneration.

Some neuroprotective agents, which block the NMDA receptor, have been studied in clinical trials in stroke patients. Dextrorphan was the first NMDA antagonist to be studied in human subjects, but is of limited use due to its side effects of hallucinations, agitation and hypotension.

Another drug, Selfotel, showed trends towards a higher mortality rate with patients treated with the drug rather than placebo, and as such the trials were halted. The drug Cerestat also had its trials terminated because of concerns with the benefit-to-risk ratio of the drug.

Clearly there is a significant requirement for an efficacious NMDA antagonist to prevent or treat neural degeneration.

Cannabinoids are a group of chemicals known to activate cannabinoid receptors in cells. These chemicals, which are found in *cannabis* plants, are also produced endogenously in humans and other animals, these are termed endocannabinoids. Synthetic cannabinoids are chemicals with similar structures to plant cannabinoids or endocannabinoids.

Plant cannabinoids can also be isolated such that they are "essentially pure" compounds. These isolated cannabinoids are essentially free of the other naturally occurring compounds, such as, other minor cannabinoids and molecules such as terpenes.

Essentially pure compounds have a degree of purity up to at least 95% by total weight. Some essentially pure cannabinoids (whether synthetic or isolated) have been suggested to be neuroprotective agents, either by direct antagonism of the NMDA receptor or by reducing the influx of calcium ions into the cell by another means such as binding with cannabinoid receptors.

It was discovered that glutamate toxicity could be prevented to some extent by isolated or synthetic tetrahydrocannabinol (THC) or cannabidiol (CBD), (Hampson et al. 1998). The cannabinoids were tested in vitro on neuronal cultures exposed to glutamate.

However further research from an in vivo study by the same group failed to find a difference between animals treated with isolated or synthetic CBD and the placebo treated animals (Rosenthal et al. 2000).

Surprisingly the applicants have found that the administration of cannabinoid-containing plant extracts, are more efficacious than essentially pure cannabinoids in the prevention of neural degeneration. In particular cannabinoid-containing plant extracts comprising as a predominant cannabinoid either tetrahydrocannabinol (THC) or cannabidiol (CBD) were particularly efficacious in the prevention of neural degeneration.

The term "cannabinoid-containing plant extract" is taken herein to refer to one or more plant extracts from the *cannabis* plant. A cannabinoid-containing plant extract contains in addition to one or more other cannabinoids, one or more non-cannabinoid components which are co-extracted with the cannabinoids from the plant material. Their respective ranges will vary according to the starting plant material and the extraction methodology used. Cannabinoid-containing plant extracts may be obtained by various means of extraction of *cannabis* plant material. Such means include but are not limited to: supercritical or subcritical extraction with $CO_2$, extraction with hot gas and extraction with solvents.

SUMMARY OF THE INVENTION

According to the first aspect of the present invention there is provided the use of one or more cannabinoid-containing plant extracts in the manufacture of a pharmaceutical formulation for use in the prevention or treatment of neural degeneration, wherein the one or more cannabinoid-containing plant extracts comprise:

i) a cannabinoid-containing fraction; and
ii) a non-cannabinoid containing fraction.

Preferably the ratio of the cannabinoid-containing fraction (i): non-cannabinoid containing fraction (ii) is between 60:40 and 90:10.

Preferably the cannabinoid-containing fraction comprises one or more of: tetrahydrocannabinol (THC); cannabidiol (CBD), cannabigerol (CBG); cannabichromene (CBC); tetrahydrocannabidivarin (THCV); tetrahydrocannabinolic acid (THCA); cannabidivarin (CBDV) and cannadidiolic acid (CBDA).

Preferably the non-cannabinoid containing fraction comprises one or more of: terpenes; sterols; triglycerides; alkanes; squalene; tocopherol; carotenoids; chlorophyll; flavonoid glycosides and alkaloids.

Naturally extracted *cannabis* plant components will be present as two different fractions: the cannabinoid-containing fraction and the non-cannabinoid containing fraction. The ratios of the two fractions are usually between 60:40 to 90:10 (cannabinoid-containing fraction: non-cannabinoid containing fraction). More preferably the ratio of the two fractions are between 70:30 to 80:20 (cannabinoid-containing fraction: non-cannabinoid containing fraction).

The cannabinoid-containing fraction will usually comprise the major cannabinoid, which is usually present at 55-80% (w/w); the minor cannabinoid, which is usually present at 0.1-6.5% (w/w); the other cannabinoids, which weight percentage usually total 4.2-17% (w/w).

The "major cannabinoid" is herein defined as the predominant cannabinoid in the cannabinoid-containing plant extract. In the case of a plant extract from a *cannabis* plant bred to contain a high content of THC the major cannabinoid will be THC.

The "minor cannabinoid" is herein defined as the second most predominant cannabinoid in the cannabinoid-containing plant extract. In the case of a plant extract from a *cannabis* plant bred to contain a high content of THC the minor cannabinoid will usually be CBD.

The "other cannabinoids" are herein defined as all of the remaining cannabinoids that are present in a *cannabis* plant extract when the major and the minor cannabinoids have been accounted for. In the case of a plant extract from a *cannabis* plant bred to contain a high content of THC the other cannabinoids will include cannabigerol (CBG), cannabichromene (CBC), tetrahydrocannabidivarin (THCV) and tetrahydrocannabinolic acid (THCA).

The non-cannabinoid containing fraction will usually comprise terpenes, which usually account for approximately 6% (w/w) of the total weight of the extract and other plant derived components, which account for 1-28% (w/w) of the total weight of the extract. The other plant derived components include sterols, triglycerides, alkanes, squalene, tocopherol and carotenoids.

The above ranges and compounds are from analysis of a cannabinoid-containing plant extract which was extracted from a *cannabis* plant using the subcritical $CO_2$ extraction technique as described in the applicants granted United Kingdom patent GB2391865.

The International patent application WO 2002/32420 in the name of Delta-9-Pharma describes in Table 1 the composition of *cannabis* plant extracts that have been extracted using other techniques. Other components of the non-cannabinoid containing fraction have been identified using supercritical $CO_2$ extraction, ethanol and hexane extraction techniques. These include: chlorophyll, flavonoid glycosides and alkaloids.

Another *cannabis* plant extraction technique is extraction with hot gas as described in the applicants granted United Kingdom patent GB2376464.

Preferably the one or more cannabinoid-containing plant extract comprises cannabidiol (CBD) as a predominant cannabinoid.

Preferably the one or more cannabinoid-containing plant extract comprises tetrahydrocannabinol (THC) as a predominant cannabinoid.

Alternatively the one or more cannabinoid-containing plant extract may comprise a combination of a CBD-containing plant extract and a THC-containing plant extract.

Preferably the cannabinoids are present as a *cannabis* based medicine extract (CBME).

A CBME is a plant extract from the *cannabis* plant and as such depending on the extraction technique used will comprise all of the "naturally extracted" *cannabis* plant components.

In one embodiment the cannabinoid-containing plant extract is packaged for delivery in a titratable dosage form.

The term "titrate" is defined as meaning that the patient is provided with a medication that is in such a form that smaller doses than the unit dose can be taken.

A "unit dose" is herein defined as a maximum dose of medication that can be taken at any one time or within a specified dosage period such as 3 hours.

Titration of doses is beneficial to the patient as they are able to increase the dose incrementally until the drug is efficacious. It is understandable that not all patients will require exactly the same dose of medication, for example patients of a larger build or faster metabolism may require a higher dose than that required by a patient that is of a smaller build. Different patients may also present with different degrees of complaints and as such may require larger or smaller doses in order to treat the complaint effectively. The benefits of a titratable dosage form over a standard dosage form, which would have to be split into a partial dose, are therefore evident.

Unit dose ranges for the cannabinoid-containing plant extract may be determined by reference to the cannabinoid content which is preferably in the range of between 5 and 100 mg of the total cannabinoids.

Preferably the pharmaceutical formulations are packaged for delivery such that delivery is targeted to an area selected from one or more of the following: sublingual; buccal; oral; rectal; nasal; parenteral and via the pulmonary system.

More preferably the pharmaceutical formulations are in the form selected from one or more of the following: gel; gel spray; tablet; liquid; capsule, by injection and for vaporisation.

Additionally the pharmaceutical formulation further comprises one or more carrier solvents. Preferably the carrier solvents are ethanol and/or propylene glycol. More preferably the ratio of ethanol to propylene glycol is between 4:1 and 1:4. More preferably still the ratio is substantially 1:1.

The term "neural degeneration" is used to describe different groups of conditions and diseases. These groups include but are not limited to: neurodegenerative diseases, ischemic diseases, brain injury or damage and age-related or autoimmune neural degeneration Neurodegenerative diseases arise when degeneration of the neural pathway occurs as a result of a specific disease. Ischemic diseases arise when degeneration of the neural pathway occurs as a result of lack of oxygen. Brain injury or damage arise when degeneration of the neural pathway occurs as a result of an injury to the brain itself. Age-related or autoimmune neural degeneration arise when degeneration of the neural pathway occurs as a result of the patient's age or due to an autoimmune disease.

The cannabinoid-containing plant extracts are used in the manufacture of a pharmaceutical formulation for use in the prevention or treatment of neurodegenerative disease.

Preferably the neurodegenerative disease is taken from the group: Alzheimer's disease; Parkinson's disease; amyotrophic lateral sclerosis; Huntington's disease; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; epilepsy or any other related neurological or psychiatric neurodegenerative disease.

The cannabinoid-containing plant extracts are used in the manufacture of a pharmaceutical formulation for use in the prevention or treatment of ischemic disease.

Preferably the ischemic disease is taken from the group: stroke; cardiac ischemia; coronary artery disease; thromboembolism; myocardial infarction or any other ischemic related disease.

The cannabinoid-containing plant extracts are used in the manufacture of a pharmaceutical formulation for use in the prevention or treatment of brain injury or damage.

Preferably the brain injury or damage is a traumatic brain injury.

A traumatic brain injury can include but is not limited to: diffuse axonal injury; concussion; contusion; whiplash or any other traumatic head or brain injury.

More preferably the brain injury or damage is an acquired brain injury.

An acquired brain injury can include but is not limited to: stroke; anoxic brain injury; hypoxic brain injury or any other acquired brain injury.

More preferably the brain injury or damage is a closed head injury or an open head injury or any other head injury.

The cannabinoid-containing plant extracts are used in the manufacture of a pharmaceutical formulation for use in the prevention or treatment of age related inflammatory or autoimmune disease.

Certain aspects of this invention are further described, by way of example only.

SPECIFIC DESCRIPTION

Recently, clinical trials have been performed on *cannabis* plant extracts, in order to test the mainly anecdotal evidence of their analgesic and other medicinal properties.

One study has found that the combination of tetrahydrocannabinol (THC) and cannabidiol (CBD) in an approximately equal ratio was an effective analgesic in patients with central neuropathic pain (Berman et al., 2004). The cannabinoid-containing plant extracts of *Cannabis Sativa* L. containing either THC or CBD were mixed in a 1:1 ratio and compared against placebo.

It has been suggested that there may be an interaction between the cannabinoid components in a *cannabis* plant extract with other non-cannabinoid components in the plant extract.

Therefore this study compared a THC-containing plant extract and a CBD-containing plant extract with their essentially pure counterparts.

The compositions of the THC-containing plant extract and the CBD-containing plant extract are described in Table 1 below.

TABLE 1

| | THC-containing plant extract (% w/w of extract) | CBD-containing plant extract (% w/w of extract) |
|---|---|---|
| Major/Minor Cannabinoid: | | |
| THC Content | 63.0-78.0 | 2.0-6.5 |
| CBD Content | 0.1-2.5 | 57.0-72.0 |
| Other Cannabinoids: | | |
| Cannabigerol | 1.0-2.0 | 0.8-6.5 |
| Cannabichromene | 0.8-2.2 | 3.0-6.5 |
| Tetrahyrocannabidivarin | 0.4-1.0 | — |
| Tetrahydrocannabinolic acid | <2.0 | — |
| Cannabidivarin | — | 1.0-2.0 |
| Cannabidiolic acid | — | 2.0 |
| Terpenes: | | |
| Monoterpenes | 0.7 | 0.4 |
| Di/tri-terpenes | 0.6 | 0.4 |
| Sesquiterpenes | 1.7 | 2.0 |
| Other terpenes | <3.0 | <3.0 |
| Other minor plant derived components including: | | |
| Sterols, Triglycerides, Alkanes, Squalene, Tocopherol, Carotenoids | 6.3-26.7 | 1.7-28.4 |

Experiments were conducted on hippocampal neurones; the effects of the cannabinoid-containing plant extracts and the essentially pure cannabinoids on calcium ion homeostasis in both acute and chronic paradigms were investigated.

Surprisingly it was discovered that there were significant differences between the cannabinoid-containing plant extracts and the essentially pure cannabinoids. The experiments on chronic application provided evidence that the essentially pure cannabinoids lost their effectiveness over a longer term, whereas the cannabinoid-containing plant extracts gained efficacy. This infers that the use of cannabinoid-containing plant extracts as neuroprotective agents is a safer and more efficacious route than the use of essentially pure cannabinoids. It would seem that one or more of the components identified in the plant extracts, including the other cannabinoids, as detailed in Table 1, contribute to the neuroprotective effects of the main cannabinoids.

In the Examples described below the following methods were used in order to elucidate the neuromodulatory effects of cannabinoids.

Culture Preparation

Standard primary hippocampal cultures were prepared from Lister-Hooded rat pups (1-3 days old), euthanised by cervical dislocation, in accordance with Home Office and institute regulations. The brain was quickly removed, hippocampi dissected out and placed in ice-cold filtered HEPES buffered solution (HBS, composition in mM: NaCl 130; KCl 5.4; $CaCl_2$ 1.8; $MgCl_2$ 1.0; HEPES 10; glucose 25). Microdissection was performed to remove blood vessels and excess, non-hippocampal, tissue.

The hippocampal tissue was thinly chopped and placed in 1 mg/ml type X and XIV protease solution (40 minutes). The tissue was then washed in HBS and triturated several times using graded fire-polished glass Pasteur pipettes. Following centrifugation, the supernatant was removed and the remaining tissue pellet re-suspended in tissue culture medium (90% Minimum Essential Medium with 10% foetal bovine serum and 2 mM L-glutamine). The tissue was stored at standard conditions: in a humidified incubator at 37° C. and in 5% $CO_2$, and re-centrifuged.

Excess medium was removed and the tissue pellet re-suspended in culture medium for plating. A drop of cell suspension was placed on the centre of a 35 mm culture dish, coated with poly-L-lysine and incubated at 37° C. for 1 hour. Following this, a further 2 ml of tissue culture medium was gently added to each dish and the culture kept in a humidified incubator (37° C.; 5% $CO_2$).

Cultures were allowed to mature for 2 days before replacement of MEM with Neurobasal Medium, supplemented with 2% B27, 2 mM L-glutamine, and 25 µM L-glutamate. Culture dishes were used for imaging at 5-10 days in vitro.

Calcium Imaging

For calcium imaging experiments, hippocampal cultures were washed with HBS at room temperature and loaded with the cell-permeable fluorescent calcium indicator Fura-2-AM (10 µM) for 1 hour in the dark.

The sodium channel blocker tetrodotoxin (TTX) was added to all perfusion media, to avoid spontaneous cell firing and transmitter release, ensuring only post-synaptic effects were visualised.

Cultures were perfused with HBS or low $Mg^{2+}$ HEPES buffered solution for experiments involving NMDA (composition in mM: NaCl 130; KCl 5.4; $CaCl_2$ 1.8; $MgCl_2$ 0.1; HEPES 10; glucose 25), at a rate of 1-2 ml/min, using a gravity perfusion system.

A suitable field of cells was identified under the microscope and a greyscale transmission image visualised and captured using Oracal software. A Xenon lamp, which gave a single wavelength of light, was used to expose the cells to 350 nm and 380 nm, specified by the monochromator.

The ratio of these wavelengths, which is directly proportional to intracellular calcium levels in the cells, was plotted after background fluorescence subtraction.

The data that were produced were pooled and means for each experiment determined.

Drugs and Stock Solutions

Essentially pure CBD and THC were stored in a 1 mg/ml ethanolic solution. For experimentation, the ethanol was evaporated off and the cannabinoid was re-suspended in DMSO (at a cannabinoid concentration of 1 mM).

*Cannabis*-containing $CO_2$ extracts of THC and CBD (obtained as per the method of GB 2391865, incorporated herein by reference) were also stored in an ethanolic solution. The THC-containing plant extract contained 72.6% THC and 2.5% CBD, whilst the CBD-containing plant extract contained 64.6% CBD and 2.5% THC. The remaining percentage of both extracts contained other cannabinoids (5-6%), terpenoids (6-7%), sterols (6%), triglycerides, alkanes, squalene, tocopherol, carotenoids and other minor, plant-derived components (qs. to 100%).

Again for experimentation, the ethanol was evaporated off and the cannabinoids re-suspended in DMSO (at a cannabinoid concentration of 1 mM).

Cannabinoid-ratioed comparators of the *cannabis*-containing plant extracts were also used in some of the experiments. The comparators comprised a ratio of essentially pure major and minor cannabinoids, but did not contain the other cannabinoids or any components of the non-cannabinoid fraction.

For the THC comparator, essentially pure THC and CBD were added together in a ratio of 29.1:1. For the CBD comparator, essentially pure CBD and THC were added together a ratio of CBD to THC of 25.9:1.

A stock of NMDA (10 mM) was made up in double-distilled water and the necessary concentrations made up in HBS. NMDA (with 100 µM glycine) was applied in every experiment to categorically distinguish between neuronal and glial cells in the image obtained.

Moreover, response to an NMDA challenge was taken as an indication of viability of neurones. In experiments that were not examining NMDA, a concentration of 50 µM was applied at the conclusion of the experiment to indicate viability.

Experimental Protocols

In order to test the regulation of calcium homeostasis in the presence of the test article, the effects were measured in response to a five-minute application of 1 µM sample.

The acute modulatory effect of calcium homeostasis was assessed by comparing an initial two-minute application of NMDA (10 µM) with a subsequent two-minute application of NMDA (10 µM). The subsequent application of the NMDA followed a five minute application of 1 µM sample.

To assess the effects of the test articles under more realistic chronic treatment regimes, cells were incubated overnight with 1 µM sample and responses to increasing doses of NMDA assessed (1, 10 & 100 µM).

In order to assess whether the acute modulatory effects are altered by overnight incubation, the cells were incubated overnight with the 1 µM sample and assessed by comparing an initial two-minute application of NMDA (10 µM) with a subsequent two-minute application of NMDA (10 µM). The subsequent application of the NMDA followed a five minute application of 1 µM test article.

Data Analysis

Fluorescent units were converted into % ΔE/F. F is defined as an average of five baseline values before drug application. The value for % ΔF/F is therefore the percentage change in the average baseline value before drug application divided by the average baseline value before drug application.

All experiments were performed a minimum of three times, each on neurones from a different culture. Only changes in fluorescence>0.1 ratio units were considered as a response. Data were exported to Excel and statistical analysis performed using Prism. Normality tests confirmed absence of normal distribution of data. Therefore, a Mann Whitney U test was utilised for paired comparisons and for multiple group comparisons a Kruskal-Wallis test with either a Dunn's or Mann Whitney post-test used.

EXAMPLE 1

The Effects of Cannabinoids on Intracellular Calcium Levels

It has previously been shown that essentially pure CBD alters the intracellular calcium levels. It has also been suggested that other cannabinoids such as essentially pure THC and the synthetic cannabinoid WIN55212-2 alter the calcium ion homeostasis in neurones. This has implications in either neuroprotection or apoptosis of the cells.

A rise in the intracellular calcium ion concentration is harmful to neurones when the increased concentration is maintained over a period of time or when the concentration exceeds physiological levels.

Calcium ion signalling constantly occurs in neurones and a transient rise in intracellular calcium ion concentration is not necessarily damaging.

The effects of the essentially pure cannabinoids, the cannabinoid-containing plant extracts and the cannabinoid-ratioed comparators were assessed to investigate the responses of the neurones to these different forms of cannabinoid.

From the previous results described above with essentially pure THC and WIN55212-2, it might be expected that all forms of cannabinoids would cause a rise in the intracellular calcium ion concentration. A smaller rise in the calcium ion concentration after treatment would indicate a better probability that this form of cannabinoid possesses neuroprotective effects.

A smaller increase in the intracellular calcium ion concentration coupled with a reduction in the concentration of calcium ions over a longer period of treatment (as detailed in Example 3) would infer that this form of cannabinoid may be useful as a neuroprotective agent.

The data generated from this experiment showed that all forms of the cannabinoids tested resulted in an increase in the concentration of intracellular calcium ions. Table 2 below details the mean size of the increases in each test article.

TABLE 2

| Test Article | Concentration of intracellular $Ca^{2+}$ | | | |
| --- | --- | --- | --- | --- |
| | Pre-treatment | Post-treatment | Response (Post-Pre) | % ΔF/F |
| P-CBD | 0.805 | 1.172 | 0.367 | 45.45 |
| E-CBD | 0.306 | 0.376 | 0.070 | 25.01 |
| C-CBD | 0.293 | 0.396 | 0.103 | 35.62 |
| P-THC | 0.363 | 0.588 | 0.225 | 56.38 |
| E-THC | 0.290 | 0.369 | 0.079 | 27.89 |
| C-THC | 0.273 | 0.633 | 0.360 | 134.14 |

In the table above the different forms of cannabinoid are abbreviated as follows:
   P-CBD—essentially pure CBD
   E-CBD—CBD-containing plant extract
   C-CBD—CBD comparator
   P-THC—essentially pure THC
   E-THC—THC-containing plant extract
   C-THC—THC comparator
   (These abbreviations are used in all of the following tables)

As can be seen in Table 2 the amount of increase in intracellular calcium ion concentration produced by the CBD- and the THC-containing plant extracts are much lower than those produced by their essentially pure counterparts.

The comparators appear to act in a similar manner to that of the essentially pure cannabinoids, causing an increase of a greater value in the concentration of the intracellular calcium ions, than that of the cannabinoid-containing plant extracts.

There doesn't appear to be any significant difference in the size of the response produced by the CBD- and the THC-containing plant extract.

As can be seen the cannabinoid-containing plant extracts produce a far smaller increase in the concentration of intracellular calcium ions inferring that these test articles would be more suitable for use as neuroprotective agents.

The reason for the cannabinoid-containing plant extracts causing a smaller increase cannot be solely due to the presence of the minor cannabinoid in the extract, (THC in the case of the CBD-containing plant extract or CBD in the case of the THC-containing plant extract), as the comparator test articles which contained the minor cannabinoid produced similar effects to that of the essentially pure cannabinoids.

It can be considered that it is the presence of one or more of the other cannabinoids or non-cannabinoid components, as detailed in Table 1, that enables the cannabinoid-containing plant extract to have a less damaging effect on the cells than the essentially pure cannabinoids.

EXAMPLE 2

The Neuromodulatory Effects of Acutely Applied Cannabinoids

The acute modulation of calcium ion homeostasis was assessed by comparing an initial two-minute application of NMDA (10 μM) with a subsequent two-minute application of NMDA following a five-minute application of 1 μM of the particular cannabinoid test article.

NMDA is a neurotoxin and is used in experiments to assess the neuroprotectivity of compounds. NMDA is a glutamate agonist and causes the neurotoxic effects associated with NMDA receptor binding.

The response produced by the cell in the presence of NMDA will be an increase in the concentration of the intracellular calcium ions. A neuroprotective agent should be able to reduce this increase.

Therefore a reduction in the size of the cells response to NMDA would infer that a test compound was neuroprotective.

The experiments described in this example compare the response produced by the cells in the presence of NMDA prior to and post treatment with the cannabinoid test article.

Table 3 below details the results obtained.

TABLE 3

| Test Article | Pre-treatment $[Ca^{2+}]$ | % ΔF/F | Post-treatment $[Ca^{2+}]$ | % ΔF/F | Response (% change) |
| --- | --- | --- | --- | --- | --- |
| P-CBD | 0.722 | 91.70 | 0.302 | 32.91 | 58.2 |
| E-CBD | 0.712 | 173.73 | 0.549 | 120.73 | 22.9 |
| C-CBD | 0.703 | 81.61 | 0.502 | 44.51 | 28.6 |
| P-THC | 0.741 | 93.69 | 0.596 | 63.81 | 19.6 |
| E-THC | 0.798 | 161.35 | 0.600 | 78.48 | 24.8 |
| C-THC | 1.082 | 133.92 | 0.737 | 59.57 | 31.9 |

As can be seen above, all of the samples were able to reduce the concentration of intracellular calcium ions, showing that they have the potential to be neuroprotective.

The essentially pure CBD was shown to produce a far greater reduction in the concentration of the intracellular calcium ions in comparison to the other test samples.

Although this response appears to show that the essentially pure CBD would be more beneficial as a neuroprotective agent than that of the other test articles, this is not necessarily the case.

Drugs that are able to strongly interfere with the action of NMDA tend to cause side effects on learning and memory. This is due to the requirement in the brain for low concentrations of glutamate for functions involved with learning and memory. When a drug is able to reduce the effects at the NMDA receptor to such a large degree although the neurones will be protected, a patient's cognition is likely to be impaired at the same time.

All of the other test articles gave similar reductions in the concentration of intracellular calcium ions of around 20-30% reduction. This reduction is more likely to be neuroprotective without harmful cognitive effects.

In this set of experiments there was little difference in the results obtained between the comparators and the cannabinoid-containing plant extracts. The essentially pure THC gave the lowest amount of reduction.

EXAMPLE 3

Long-Term Action of Cannabinoids on the Intracellular Calcium Ion Concentration

In order to assess the chronic effects of the different forms of cannabinoids on the intracellular calcium ion concentration, cells were incubated overnight with 1 µM of the test article at 37° C., 5% $CO_2$. Responses to increasing doses of NMDA (1, 10 & 100 µM) were assessed.

Because the treatment of neurodegenerative diseases is very likely to require more than one dose of medication an assessment of the effects of the cannabinoids over a longer-term was made.

A reduction in the intracellular calcium ion concentration would infer that the cannabinoid had neuroprotective effects.

The concentration of intracellular calcium ions was measured in the cells prior to treatment, to determine the effect that the test article made to the concentration when incubated overnight.

This data is shown in Table 4 below and can be compared with the data produced from the acute treatment with the different forms of cannabinoids as described in Example 1 (Table 2).

The controls that were used were naïve culture dishes with no incubation with test article; the NMDA was added at the appropriate concentration and the change in the concentration of intracellular calcium ions was determined.

TABLE 4

| Test Article | Concentration of intracellular $Ca^{2+}$ Response (Post-Pre) | Change from control (%) |
|---|---|---|
| Control | 0.775 | — |
| P-CBD | 0.893 | 13.2 |
| E-CBD | 0.786 | 1.4 |
| C-CBD | 0.919 | 15.7 |
| P-THC | 0.826 | 6.2 |
| E-THC | 0.751 | −3.2 |
| C-THC | 0.814 | 4.8 |

A smaller percentage change from the control value demonstrates a smaller increase in the concentration of intracellular calcium ions. A minus figure for the percentage change from the control value demonstrates a reduction in the concentration of calcium ions.

As detailed in the table above, it can be seen that the CBD-containing plant extract produced a far smaller change in the intracellular calcium ion concentration than that produced by the essentially pure CBD and the CBD comparator. The change in concentration of intracellular calcium ions that was produced by the CBD-containing plant extract was of a similar level to that produced by the control.

The THC-containing plant extract was shown to reduce the concentration of the intracellular calcium ions, whereas incubation with the essentially pure THC and the THC comparator both resulted in an increase that was not as large as the increase produced by the essentially pure CBD and CBD comparator.

These data are very important as they show that the cannabinoid-containing plant extracts do not cause a significant alteration in the neurones basal calcium ion concentration.

When these data are compared to that in Table 2 (Example 1) where the acute application of all of the test articles resulted in an increase in the concentration of intracellular calcium ions, it can be seen that the use of cannabinoid-containing plant extracts, as a longer-term treatment would not interfere with cell signalling.

The essentially pure cannabinoids and the comparators could potentially cause apoptosis or cellular damage when used as a longer-term treatment as the chronically raised intracellular calcium ion concentrations produced by overnight incubation with these cannabinoids is known to be harmful.

The effect of increasing concentrations of the neurotoxin NMDA on the concentration of intracellular calcium ions was also assessed.

Tables 5 to 7 below detail the cells responses to the different concentrations of NMDA. A reduction in the concentration of intracellular calcium ions would infer that the test article that the cells were incubated with overnight was able to produce neuroprotective effects in the neurones.

TABLE 5

1 µM NMDA

| Test Article | Concentration of intracellular $Ca^{2+}$ | | | |
|---|---|---|---|---|
| | Pre-treatment | Post-treatment | Response (Post-Pre) | %ΔF/F |
| P-CBD | 0.933 | 0.410 | −0.523 | 43.80 |
| E-CBD | 0.778 | 0.221 | −0.557 | 27.33 |
| C-CBD | 0.967 | 0.417 | −0.550 | 41.47 |
| P-THC | 0.839 | 0.522 | −0.317 | 62.24 |
| E-THC | 0.746 | 0.135 | −0.611 | 18.13 |
| C-THC | 0.811 | 0.492 | −0.319 | 60.70 |

As is shown in Table 5 above, all of the test articles reduced the concentration of intracellular calcium ions after treatment with 1 µM NMDA. All of the test articles reduced the concentration to a similar degree apart from the essentially pure THC and the THC comparator. These samples did not reduce the concentration of calcium ions as much as the others.

From these data, at the lowest concentration of NMDA tested, all of the test articles show potential for neuroprotectivity. When these data are combined with the data from Table 4 it is clear that only the cannabinoid-containing plant extracts would be useful, as they did not raise the intracellular calcium ion concentration on long-term treatment, whereas the other test articles did.

TABLE 6

10 µM NMDA

| Test Article | Concentration of intracellular $Ca^{2+}$ | | | |
|---|---|---|---|---|
| | Pre-treatment | Post-treatment | Response (Post-Pre) | %ΔF/F |
| P-CBD | 0.913 | 0.489 | −0.424 | 53.54 |
| E-CBD | 0.813 | 0.491 | −0.322 | 60.35 |
| C-CBD | 1.048 | 0.495 | −0.533 | 47.24 |
| P-THC | 0.866 | 0.498 | −0.368 | 57.50 |

TABLE 6-continued

10 μM NMDA

Concentration of intracellular Ca$^{2+}$

| Test Article | Pre-treatment | Post-treatment | Response (Post-Pre) | %ΔF/F |
|---|---|---|---|---|
| E-THC | 0.802 | 0.842 | 0.040 | 104.98 |
| C-THC | 0.861 | 0.578 | −0.283 | 67.12 |

As is described in Table 6 all of the test articles, except the THC-containing plant extract resulted in a decrease in the concentration of intracellular calcium ions. The amount of reduction shown by all of the other test articles was similar to that shown at the NMDA concentration of 1 μM.

As noted above when these data are compared with the data from Table 4 the CBD-containing plant extract that would be of benefit as a neuroprotectant at this higher concentration of NMDA.

TABLE 7

100 μM NMDA

Concentration of intracellular Ca$^{2+}$

| Test Article | Pre-treatment | Post-treatment | Response (Post-Pre) | %ΔF/F |
|---|---|---|---|---|
| P-CBD | 0.910 | 1.289 | 0.379 | 141.57 |
| E-CBD | 0.881 | 1.004 | 0.123 | 114.01 |
| C-CBD | 1.148 | 1.404 | 0.256 | 122.31 |
| P-THC | 0.947 | 1.897 | 0.950 | 200.35 |
| E-THC | 0.872 | 2.578 | 1.706 | 295.77 |
| C-THC | 0.942 | 1.599 | 0.657 | 169.76 |

At the highest concentration of NMDA none of the test articles were able to reduce the concentration of intracellular calcium ions. This result is not unsurprising as a concentration of 100 μM NMDA is extremely neurotoxic and can result in immediate cell death. At the lower concentrations of NMDA there is neural degeneration and possibly delayed apoptosis.

EXAMPLE 4

Acute Effects of Cannabinoids on NMDA Calcium Ion Response Following Overnight Incubation In order to assess whether the neuroprotective effects elicited by the test articles in Example 2 (Table 3) were altered by the overnight incubation with the different forms of cannabinoids the following experiments were undertaken. It has been speculated previously that the cannabinoid receptors can become desensitised when exposed to their agonist for a longer period of time.

The hippocampal neurones were incubated overnight with 1 μM test article. The neurotoxin NMDA was then applied at a concentration of 10 μM for 2 minutes; this was then followed by a 5 minute application of 1 μM of the same test article.

Table 8 details the concentrations of intracellular calcium ions when treated with the different forms of cannabinoids. Similarly to the effects described in Example 2 a reduction in the concentration of intracellular calcium ions would infer that the test article had a neuroprotective effect. The CBD and THC comparators were not tested in this experiment.

TABLE 8

| Test Article | Pre-treatment [Ca$^{2+}$] | %ΔF/F | Post-treatment [Ca$^{2+}$] | %ΔF/F | Response (% change) |
|---|---|---|---|---|---|
| P-CBD | 0.424 | 52.42 | 0.715 | 71.97 | −68.6 |
| E-CBD | 0.662 | 77.63 | 0.336 | 32.43 | 49.2 |
| P-THC | 0.379 | 46.53 | 0.487 | 38.93 | −28.5 |
| E-THC | 0.843 | 112.08 | 0.680 | 62.11 | 19.3 |

As can be seen in the table above, both of the essentially pure cannabinoids resulted in an increase in the concentration of the intracellular calcium ions. The essentially pure CBD increased the concentration to a large extent and one which itself could be seen to be neurotoxic rather than neuroprotective. This is surprising as in Example 2; the essentially pure CBD produced the largest reduction in the concentration of intracellular calcium ions.

Both the CBD- and the THC-containing plant extract reduced the concentration of intracellular calcium ions. This very clearly shows that the cannabinoid-containing plant extracts have a far greater potential to be neuroprotective agents.

CONCLUSION

The data generated by the series of experiments described in the accompanying examples provide clear evidence that the cannabinoid-containing plant extracts are more efficacious than their essentially pure counterparts.

Furthermore the data from the cannabinoid comparator samples provides evidence that the reason for the improved effectiveness of the cannabinoid-containing extracts over the essentially pure cannabinoids is not purely due to the presence of the minor (or second most predominant) cannabinoid in the cannabinoid-containing plant extract.

It would appear that the increased efficacy of the cannabinoid-containing plant extracts is as a result of the presence of one or more of the other components identified in the plant extracts. These other components include, but are not limited to, the other cannabinoids or constituents of the non-cannabinoid fraction, as detailed in Table 1.

The invention claimed is:

1. A method of treating a patient suffering from an acquired brain injury consisting essentially of administering to said patient a therapeutically effective amount of a pharmaceutical formulation consisting essentially of an extract of *Cannabis sativa*, and wherein the extract of *Cannabis sativa* is obtained by supercritical or subcritical extraction with CO2, and is either (a) a *Cannabis sativa* L. plant extract where a major cannabinoid is tetrahydrocannabinol (THC), and the extract consists essentially of i) from 67.3-87.7% (w/w) of cannabinoid-containing components consisting essentially of the major cannabinoid; a minor cannabinoid; and one or more other cannabinoids; and ii) from 12.3-32.7% (w/w) of non-cannabinoid components consisting essentially of terpenes; sterols; triglycerides; alkanes; squalene; tocopherol; carotenoids; chlorophyll; flavonoid; glycosides and alkaloids, or (b) a *Cannabis sativa* L. plant extract where a major cannabinoid is cannabidiol (CBD) and the extract consists essentially of i) from 65.8-95.5% (w/w) of cannabinoid-containing components consisting essentially of the major cannabinoid; a minor cannabinoid; and one or more other cannabinoids; and ii) from 7.5-34.2% (w/w) of non-cannabinoid components consisting essentially of terpenes; sterols; triglycerides;

alkanes; squalene; tocopherol; carotenoids; chlorophyll; flavonoid; glycosides and alkaloids, wherein the acquired brain injury is effectively treated.

* * * * *